(12) United States Patent
Ba et al.

(10) Patent No.: US 10,139,326 B2
(45) Date of Patent: Nov. 27, 2018

(54) DETERMINING THE LIFE SPAN OF AN ELASTOMER IN A MOTOR

(71) Applicant: SCHLUMBERGER TECHNOLOGY CORPORATION, Sugar Land, TX (US)

(72) Inventors: Samba Ba, Katy, TX (US); Anton Kolyshkin, Katy, TX (US)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 107 days.

(21) Appl. No.: 15/220,269

(22) Filed: Jul. 26, 2016

(65) Prior Publication Data

US 2017/0030184 A1 Feb. 2, 2017

Related U.S. Application Data

(60) Provisional application No. 62/197,473, filed on Jul. 27, 2015.

(51) Int. Cl.
*G01N 3/12* (2006.01)
*E21B 4/02* (2006.01)

(52) U.S. Cl.
CPC ...... *G01N 3/12* (2013.01); *E21B 4/02* (2013.01)

(58) Field of Classification Search
CPC .................................... G01N 3/12; E21B 4/02
See application file for complete search history.

(56) References Cited

U.S. PATENT DOCUMENTS

| | | | |
|---|---|---|---|
| 6,282,403 B1 * | 8/2001 | Spencer | B65H 20/02 100/47 |
| 2010/0038142 A1 * | 2/2010 | Snyder | E21B 4/02 175/107 |
| 2015/0022051 A1 * | 1/2015 | Meng | F04C 2/1075 310/216.001 |
| 2015/0167466 A1 * | 6/2015 | Teodorescu | E21B 47/01 175/40 |

FOREIGN PATENT DOCUMENTS

| WO | 2010043951 A2 | 4/2010 |
|---|---|---|
| WO | 2013185005 A2 | 12/2013 |

* cited by examiner

*Primary Examiner* — Nicholas Tobergte

(57) ABSTRACT

A method for determining a remaining life span of an elastomer in a motor. The method includes running a downhole tool into a wellbore. The downhole tool includes a mud motor having a rotor and a stator. At least one of the rotor or the stator includes, or is at least partially made from, an elastomer. A number of cycles before the elastomer fails may be predicted. A number of cycles during a time period may be determined. A change in a remaining life span of the elastomer over the time period may be determined, based upon the number of cycles before the elastomer fails and the number of cycles during the time period.

20 Claims, 4 Drawing Sheets

DETERMINING THE LIFE SPAN OF AN ELASTOMER IN A MOTOR

CROSS-REFERENCE TO RELATED APPLICATIONS

This application claims the benefit of U.S. Provisional Patent Application having Ser. No. 62/197473, filed on Jul. 27, 2015, entitled "Determining the Life Span of an Elastomer in a Motor," the disclosure of which is incorporated by reference herein in its entirety.

BACKGROUND

A mud motor is a component in a downhole tool that uses hydraulic power from fluid flowing therethrough to drive a drill bit. The mud motor may include a power section made up of a stator and a rotor. The stator may be constructed from an elastomer, and the rotor may be constructed from a metal. In the power section of the mud motor, the elastomer of the stator tends to be the weakest link, in terms of number of operational hours before failure. The elastomer may be rated by the manufacturer for a predetermined number of operating hours before failure (e.g., 50 hours). As will be appreciated, however, the elastomer may fail before or after the predetermined number of hours depending upon speed (e.g., RPM), temperature, pressure, and the like.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

A method for determining a remaining life span of an elastomer in a motor is disclosed. The method includes running a downhole tool into a wellbore. The downhole tool includes a mud motor, and the mud motor includes a rotor and a stator. The rotor, the stator, or both includes or is at least partially made from an elastomer. A number of cycles before the elastomer fails may be predicted. A number of cycles during a time period may be determined. A change in a remaining life span of the elastomer over the time period may be determined, based upon the number of cycles before the elastomer fails and the number of cycles during the time period.

In another embodiment, the method includes running a downhole tool into a wellbore. The downhole tool includes a mud motor, and the mud motor includes a rotor and a stator. The rotor, the stator, or both includes or is at least partially made from an elastomer. A differential pressure is measured across the mud motor. A temperature is measured proximate to the mud motor. A number of cycles before the elastomer fails is determined based at least partially upon the differential pressure and the temperature.

A computing system is also disclosed. The computing system includes a processor and a memory system. The memory system includes a non-transitory computer-readable medium storing instructions that, when executed by the processor, causes the computing system to perform operations. The operations include predicting a number of cycles before an elastomer in a downhole tool fails. The operations also include determining a number of cycles during a time period. The operations also include determining a change in a remaining life span of the elastomer over the time period, based upon the number of cycles before the elastomer fails and the number of cycles during the time period.

BRIEF DESCRIPTION OF THE DRAWINGS

So that the recited features may be understood in detail, a more particular description, briefly summarized above, may be had by reference to one or more embodiments, some of which are illustrated in the appended drawings. It is to be noted, however, that the appended drawings are illustrative embodiments, and are, therefore, not to be considered limiting of its scope.

DETAILED DESCRIPTION

Figure 1:
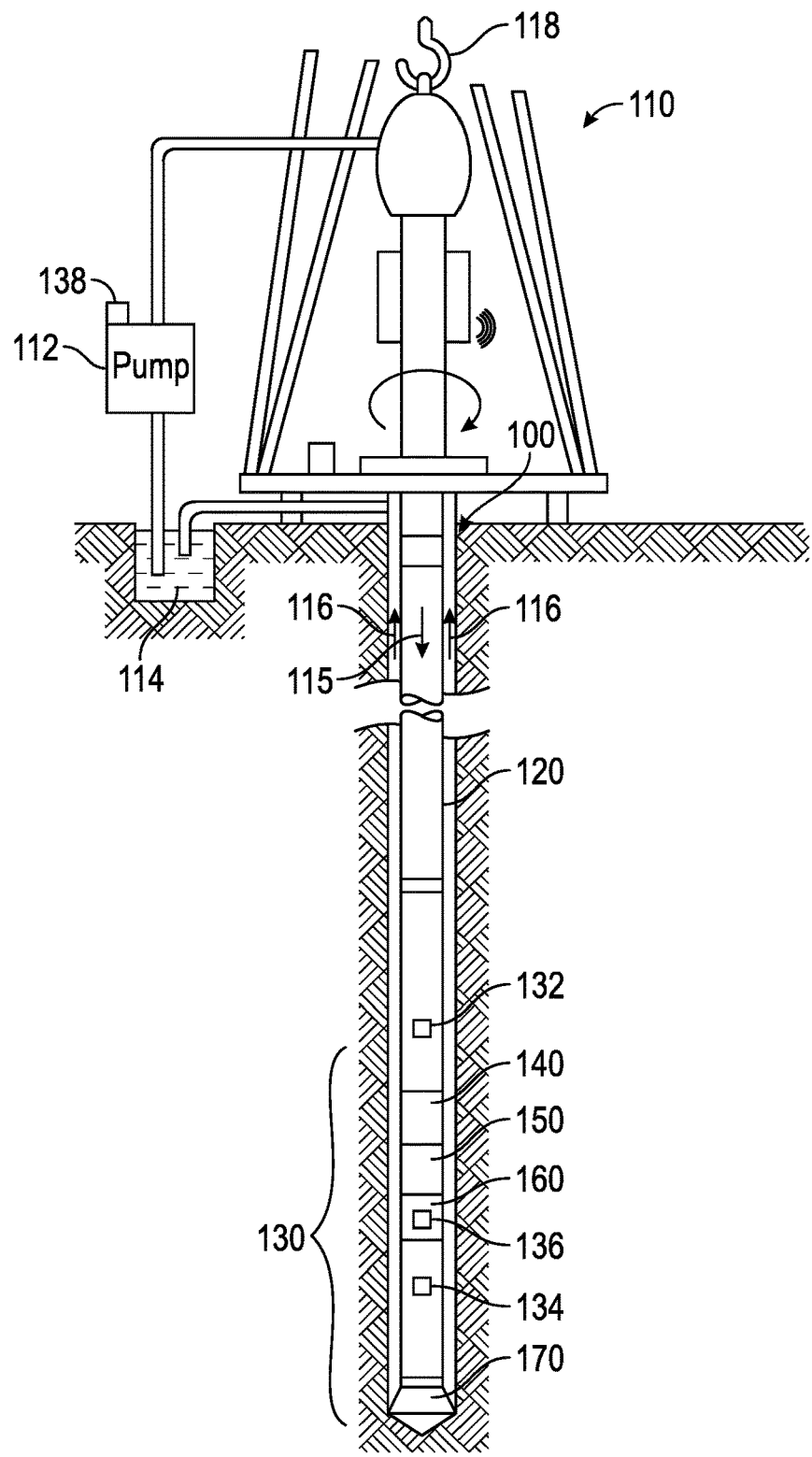
FIG. 1 depicts a cross-sectional view of an illustrative downhole tool in a wellbore, according to an embodiment.

FIG. 1 depicts a cross-sectional view of an illustrative downhole tool 130 in a wellbore 100, according to an embodiment. The downhole tool 130 may be run into the wellbore 100 on a drill string 120 that extends downward from a derrick assembly 110. The downhole tool 130 may be or include a bottom hole assembly ("BHA") that includes a logging-while-drilling ("LWD") module 140, a measuring-while-drilling ("MWD") module 150, a mud motor 160, and drill bit 170.

The LWD module 140 may be configured to measure one or more formation properties as the wellbore 100 is being drilled or at any time thereafter. The formation properties may include resistivity, porosity, sonic velocity, gamma ray, and the like. The MWD module 150 may be configured to measure one or more physical properties as the wellbore 100 is being drilled or at any time thereafter. The physical properties may include pressure, temperature, wellbore trajectory, a weight-on-bit, torque-on-bit, vibration, shock, stick slip, and the like.

A pump 112 at the surface may cause a drilling fluid 114 to flow through the interior of the drill string 120, as indicated by the directional arrow 115. The drilling fluid 114 may flow through the mud motor 160, which may cause the mud motor 160 to drive the drill bit 170. After passing through the mud motor 160, the drilling fluid 114 may flow out of the drill bit 170 and then circulate upwardly through the annulus between the outer surface of the drill string 120 and the wall of the wellbore 100, as indicated by the directional arrows 116.

Figure 2:
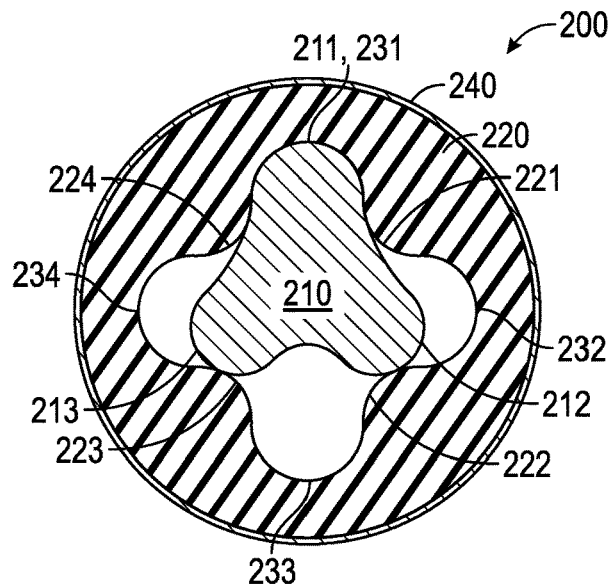
FIG. 2 depicts a cross-sectional view of a power section of an illustrative mud motor in the downhole tool, according to an embodiment.

FIG. 2 depicts a cross-sectional view of a power section 200 of the mud motor 160, according to an embodiment. The power section 200 may include a rotor 210 positioned within a stator 220. A housing 240 may at least partially surround the stator 220. The rotor 210 may include one or more lobes (three are shown: 211-213), and the stator 220 may include one or more lobes (four are shown: 221-224). In at least one embodiment, the stator 220 has one more lobe 221-224 than the rotor 210. Recesses 231-234 may be formed in the stator 220 between each pair of adjacent lobes 221-224. As the rotor 210 rotates within the stator 220, the lobes 211-213 of the rotor 210 may be inserted into and then withdrawn from recesses 231-234 in the stator 220. This may cause the rotation of the rotor 210 to be eccentric.

The rotor 210 may be made from one or more metals, and at least a portion of the stator 220 may be made from one or more elastomers. For example, the inner surface of the stator 220 that contacts the rotor 210 may be made from the elastomer. Although not shown, in another embodiment, the outer surface of the rotor 210 may be made from one or more elastomers, and/or the stator 220 may be made from one or more metals. Illustrative elastomers may include rubbers such as HR and the like, as well as other rubbers known to those skilled in the art.

Figure 3:
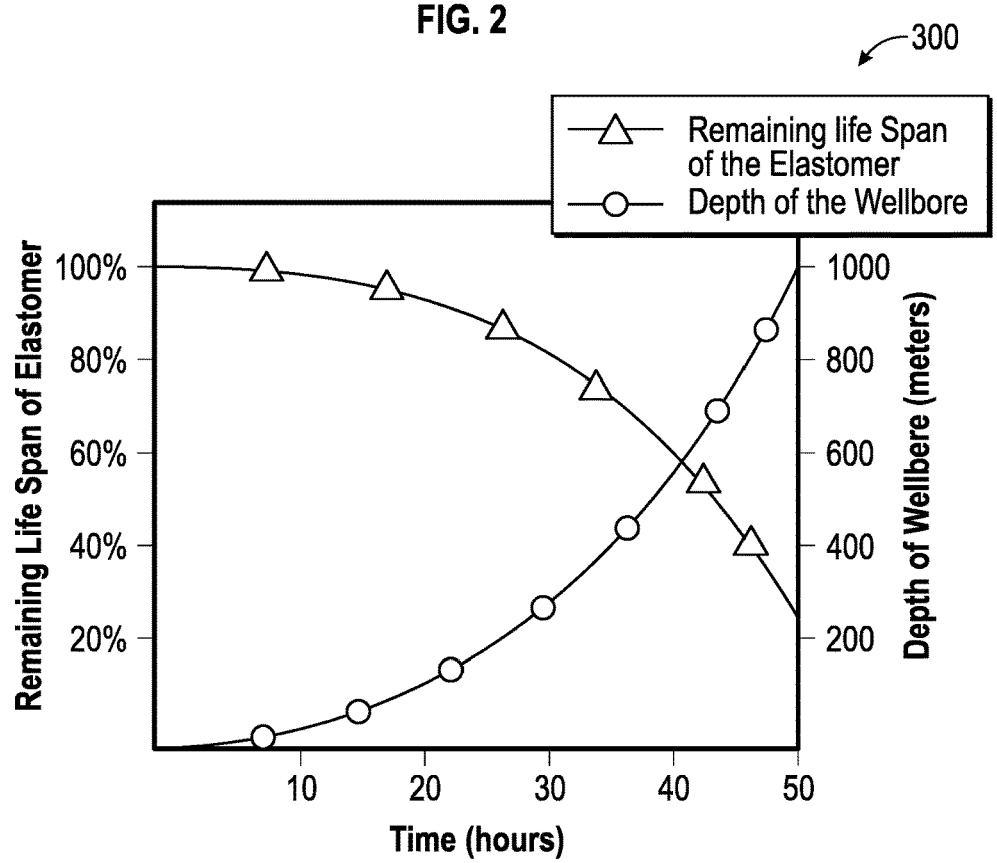
FIG. 3 depicts a graph showing an example of the life span of an elastomer in the mud motor versus time and the depth of the downhole tool (which includes the mud motor) in the wellbore versus time, according to an embodiment.

FIG. 3 depicts an illustrative graph 300 showing a life span of the elastomer in the mud motor 160 versus time, according to an embodiment. As the downhole tool 130 drills the wellbore 100, the life span of the elastomer in the mud motor 160 decreases. When the life span of the elastomer reaches 0%, the mud motor 160 may no longer function. In the embodiment shown, the rate that the life span of the elastomer decreases is greater during the last 10 hours of drilling (e.g., from t=40 to t=50) than during the first 10 hours of drilling (e.g., from t=0 to t=10).

The graph 300 also shows the depth of the downhole tool 130 (which includes the mud motor 160) in the wellbore 100 versus time. As the downhole tool 130 drills the wellbore 100, the depth of the wellbore 100 increases. In the embodiment shown, the rate that the depth of the wellbore 100 increases is greater during the last 10 hours of drilling (e.g., from t=40 to t=50) than during the first 10 hours of drilling (e.g., from t=0 to t=10). Thus, as may be seen, the rate that the life span of the elastomer decreases over time may correspond (e.g., directly) to the rate that the depth of the wellbore increases overtime. The rate that the depth of the wellbore changes with respect to the change in time may be referred to as the rate of penetration ("ROP").

Figure 4:
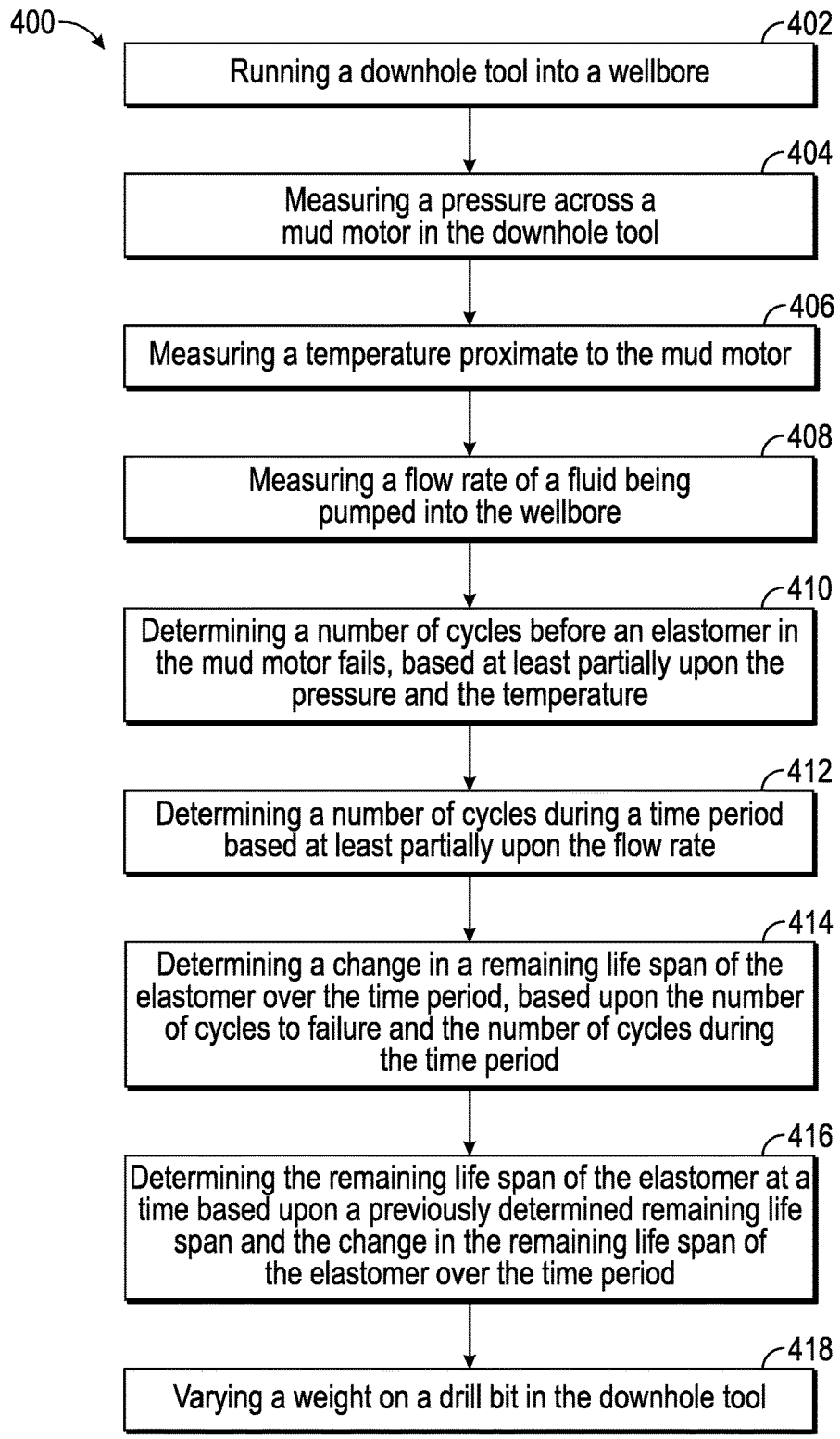
FIG. 4 depicts a flow chart of a method for determining a remaining life span of an elastomer in a power section of a mud motor, according to an embodiment.

FIG. 4 depicts a flow chart of a method 400 for determining a remaining life span of an elastomer in a power section 200 of a mud motor 160, according to an embodiment. The method 400 may begin by running the downhole tool 130 into the wellbore 100, as at 402. The downhole tool 130 may include the mud motor 160.

The method 400 may also include measuring a pressure across the mud motor 160, as at 404. The measurements may be taken by one or more pressure sensors (two are shown in FIG. 1 at 132, 134) coupled to the downhole tool 130. For example, the first pressure sensor 132 may be positioned on a first side of the mud motor 160 (e.g., above the mud motor 160), and the second pressure sensor 134 may be positioned on a second side of the mud motor 160 (e.g., below the mud motor 160). In at least one embodiment, the differential pressure may be obtained as the difference between on-bottom and off-bottom pressure. Comparing the measurements obtained by the first and second pressure sensors 132, 134 when the drill bit 170 is on-bottom and off-bottom may yield the differential pressure across the mud motor 160. Instead of, or in addition to, the pressure differential across the mud motor 160, in some embodiments, the surface internal pressure may be used. The surface internal pressure may be measured in the standpipe.

The method 400 may also include measuring a temperature proximate to the mud motor 160, as at 406. The measurement may be taken by one or more temperature sensors (one is shown in FIG. 1 at 136) coupled to the downhole tool 100. For example, the temperature sensor 136 may be coupled to the LWD module 140, the MWD module 150, the mud motor 160, or proximate to any one of those components. As used herein, the term "proximate to" refers to within 30 meters or less. The temperature may also be predicted based on formation and drilling depth.

The method 400 may also include measuring a flow rate of a fluid being pumped into the wellbore 100 from the surface (e.g., by the pump 112), as at 408. The measurement may be taken by one or more flow rate sensors (one is shown in FIG. 1 at 138) coupled to the pump 112, the LWD module 140, the MWD module 150, the mud motor 160, or proximate to any one of those components. In some embodiments, the method 400 may be performed without measuring or determining the speed (e.g., RPM) of the mud motor 160.

The method 400 may also include determining (e.g., estimating or predicting) a number of cycles before the elastomer in the mud motor 160 fails based at least partially upon the pressure and the temperature, as at 410. As used herein, the "number of cycles" refers to the number of times that one (or each) of the lobes 221-224 of the stator 220 is contacted by one (or each) of the lobes 211-213 of the rotor 210. In at least one embodiment, the number of cycles may be equal to the number of lobes 211-213 on the rotor 210 multiplied by the number of revolutions of the rotor 210. Referring to the example shown in FIG. 2, there may be three cycles in each full revolution of the rotor 210. In one example, the number of cycles before the elastomer fails may be determined by:

$$N_{fail} = f(W, E_{cr}) \quad (1)$$

$N_{fail}$ represents the number of cycles to failure, W represents the maximum strain energy density of the elastomer, and $E_{cr}$ represents the critical tearing energy of the elastomer. The strain energy density (W) may at least partially depend on the fit between the rotor 210 and the stator 220, the type of elastomer, the pressure differential across the mud motor 160 (e.g., measured by the pressure sensors 132, 134), the temperature measured proximate to the mud motor 160 (e.g., by the temperature sensor 136), the flow rate of the fluid being pumped into the wellbore 100 from the surface (e.g., measured by the flow rate sensor 138), the type of fluid being pumped into the wellbore 100 from the surface, or a combination thereof The critical tearing energy ($E_{cr}$) may at least partially depend on the type of the fluid pumped into the wellbore from the surface, the type of elastomer, the temperature measured proximate to the mud motor 160 (e.g., by the temperature sensor 136), or a combination thereof.

The pressure differential P and the temperature T effects may be solved using an FEA solver. The results from the FEA solver may be stored in the database. After that, when the temperature and pressure are measured, the maximum strain energy density W and the critical tearing energy $E_{cr}$ may be de-rated or up-rated depending on the values of P and T In one example, $f(W, E_{cr})$ may be determined by:

$$f(W, E_{cr}) = \frac{1}{r_c(F-1)} \left(\frac{E_{cr}}{2kW}\right)^F c_0^{F-1} \quad (2)$$

f represents the remaining life span of the elastomer (i.e., the fatigue life), $c_0$ represents the estimated flaw size of the elastomer, $r_c$ represents a parameter from the Thomas fatigue model, and k represents a volumetric constant. F, $c_0$, $r_c$, and k may at least partially depend on the type of elastomer, the pressure differential across the mud motor 160 (e.g., measured by the pressure sensors 132, 134), the temperature measured proximate to the mud motor 160 (e.g., measured by the temperature sensor 136), the duration for which the elastomer is exposed to the pressures and temperatures, or a combination thereof The remaining life span of the elastomer (F) may be a percentage value from 0 to 1 (e.g., from 0% to 100%).

In at least one embodiment, determining the number of cycles before the elastomer in the mud motor 160 fails ($N_{fail}$) may include referencing a library. The library may include a plurality of measured or simulated $N_{fail}$ values. The library may output, or the user may select, an $N_{fail}$ value that best corresponds with one or more known or measured input values such as the pressure measured by the pressure sensors 132, 134, the temperature measured by the temperature sensor 136, the type of drilling fluid being pumped into the wellbore 100, $c_0$, $r_c$, k, or a combination thereof.

The method 400 may then include determining a number of cycles during a time period t based at least partially upon the flow rate of the fluid being pumped into the wellbore 100, as at 412. The time in t may refer to the overall drilling time or the time in which the fluid is pumped into the wellbore 100 from the surface. t may be selected to be small enough so that the speed of the mud motor 160, the pressure differential across the mud motor 160 (e.g., measured by the pressure sensors 132, 134), the temperature proximate to the mud motor 160 (e.g., by the temperature sensor 136), the flow rate of the fluid pumped into the wellbore 100 (e.g., measured by the flow rate sensor 138), the type of fluid being pumped into the wellbore 100, or a combination thereof, do not vary by more than about 10% during t. For example, t may be from about 1 minute to about 5 minutes, about 5 minutes to about 15 minutes, about 15 minutes to about 30 minutes, about 30 minutes to about 1 hour, about 1 hour to about 5 hours, or more.

In one example, the number of cycles during the time period t may be determined by:

$$N_{current} = g(\text{flow}(t)) \times t \times r \quad (3)$$

$N_{current}$ represents the number of cycles during the time period (t), g represents the estimated cycle time or RPM, flow(t) represents the mean flow rate at the time t, and r represents the number of lobes 211-213 on the rotor 210.

g(flow (t)) may be derived using one or more power curves that are stored in the library discussed above or a different library. The power curves may be generated using actual measurements, or they may be simulated. The power curves may include the differential pressure across the mud motor 160 (e.g., on the X axis) versus the speed of the mud motor 160 in RPM (e.g., on the Y axis). The power curves may also include the differential pressure across the mud motor 160 (e.g., on the X axis) versus the torque of the mud motor 160 (e.g., on the Y axis).

The method 400 may then include determining the change in the remaining life span of the elastomer (F) over the time period (t) based upon the number of cycles to failure ($N_{fail}$) and the number of cycles ($N_{current}$) during the time period (t), as at 414. More particularly, the change in the remaining life span of the elastomer (F) over the time period (t) may be determined by:

$$F = \frac{N_{current}}{N_{fail}} \quad (4)$$

The method 400 may then include determining the remaining life span of the elastomer (F) at a time (t) based upon a previously determined remaining life span ($F_{previous}$) and the change in the remaining life span of the elastomer (F) over the time period (t), as at 416. This may be done substantially in real-time using the measurements above. The previously determined remaining life span ($F_{previous}$) may be determined at time (t t) using the same method 400. More particularly, the remaining life span of the elastomer (F) at a time (t) may be determined by:

$$F = F_{previous} F \quad (5)$$

EXAMPLE 1

Referring to FIGS. 3 and 4, a user may want to determine the remaining life span (F) of the elastomer at time t=20 hours. $N_{fail}$ may be 100,000, N current may be 5,000, and t may be 5 hours. The previously determined remaining life span ($F_{previous}$) (e.g., at time t=15 hours) may be 0.95 or 95%. The change in the remaining life span of the elastomer (F) over the time period (5 hours) may be 5,000/100,000=0.05 or 5%. Thus, the remaining life span of the elastomer (F) at a time t=20 hours may be 0.90 or 90%.

EXAMPLE 2

Referring again to FIGS. 3 and 4, the user may want to determine the remaining life span (F) of the elastomer at time t=40 hours. $N_{fail}$ may be still be 100,000, N current may be 10,000, and t may still be 5 hours. The previously determined remaining life span ($F_{previous}$) (e.g., at time t=35 hours) may be 0.70 or 70%. The change in the remaining life span of the elastomer (F) over the time period (5 hours) may be 10,000/100,000=0.10 or 10%. Thus, the remaining life span of the elastomer (F) at a time t=40 hours may be 0.60 or 60%.

Referring back to FIG. 4, the method 400 may also include varying the weight on the drill bit 170 in response to the change in the remaining life span of the elastomer (F) over the time period (t) and/or the remaining life span of the elastomer (F), as at 418. In one embodiment, the user may vary the weight on the drill bit 170 by varying the weight on the hook 118 (see FIG. 1). This may increase or decrease the torque generated by the mud motor 160. Increasing the weight on the drill bit 170 (and the torque generated by the mud motor 160) may increase the rate of penetration of the downhole tool 130 in the wellbore 100. However, this may also increase the rate at which the remaining life span of the elastomer decreases. Decreasing the weight on the drill bit 170 (and the torque of the mud motor 160) may decrease the rate of penetration of the downhole tool 130 in the wellbore 100. This may decrease the rate at which the remaining life span of the elastomer decreases.

With this in mind, the user may be able to balance the remaining life span of the elastomer (F) against the time to reach the desired depth. For example, referring again to FIG. 3, the desired depth of the wellbore 100 may be 1000 meters. At time t=20 hours, the user may receive results indicating that the remaining life span of the elastomer (F) is about 90%, and the current depth of the wellbore 100 is about 200 meters. Realizing that the downhole tool 130 is on pace to reach the desired depth when the remaining life span of the elastomer (F) is about 50%, the user may then increase the weight on the drill bit 170 to increase the torque on the mud motor 160 and the rate of penetration of the downhole tool 130 in the wellbore 100. As seen in FIG. 3, this may allow the user to reach the desired depth in a shorter period of time with the remaining life span of the elastomer (F) still being greater than 0%.

If, however, at time t=20 hours, the user receives results indicating that the remaining life span of the elastomer (F) is about 50%, and the current depth of the wellbore 100 is about 400 meters, the user may realize that the remaining life span of the elastomer (F) may reach 0% before the desired depth is reached. If this occurs, the downhole tool 130 may be raised to the surface to replace the mud motor 160, which is a time-consuming process. Rather than allow this to occur, the user may simply reduce the weight on the drill bit 170. This may decrease the torque on the mud motor 160 and decreases the rate of penetration of the downhole tool 130 in the wellbore 100. Although the rate of penetration may be slower, the overall time to reach the desired depth may still be faster than if the user has to to pull the downhole tool 130 out of the wellbore 100, replace the elastomer, and run the downhole tool 130 back into the wellbore 100 to finish drilling.

Figure 5:
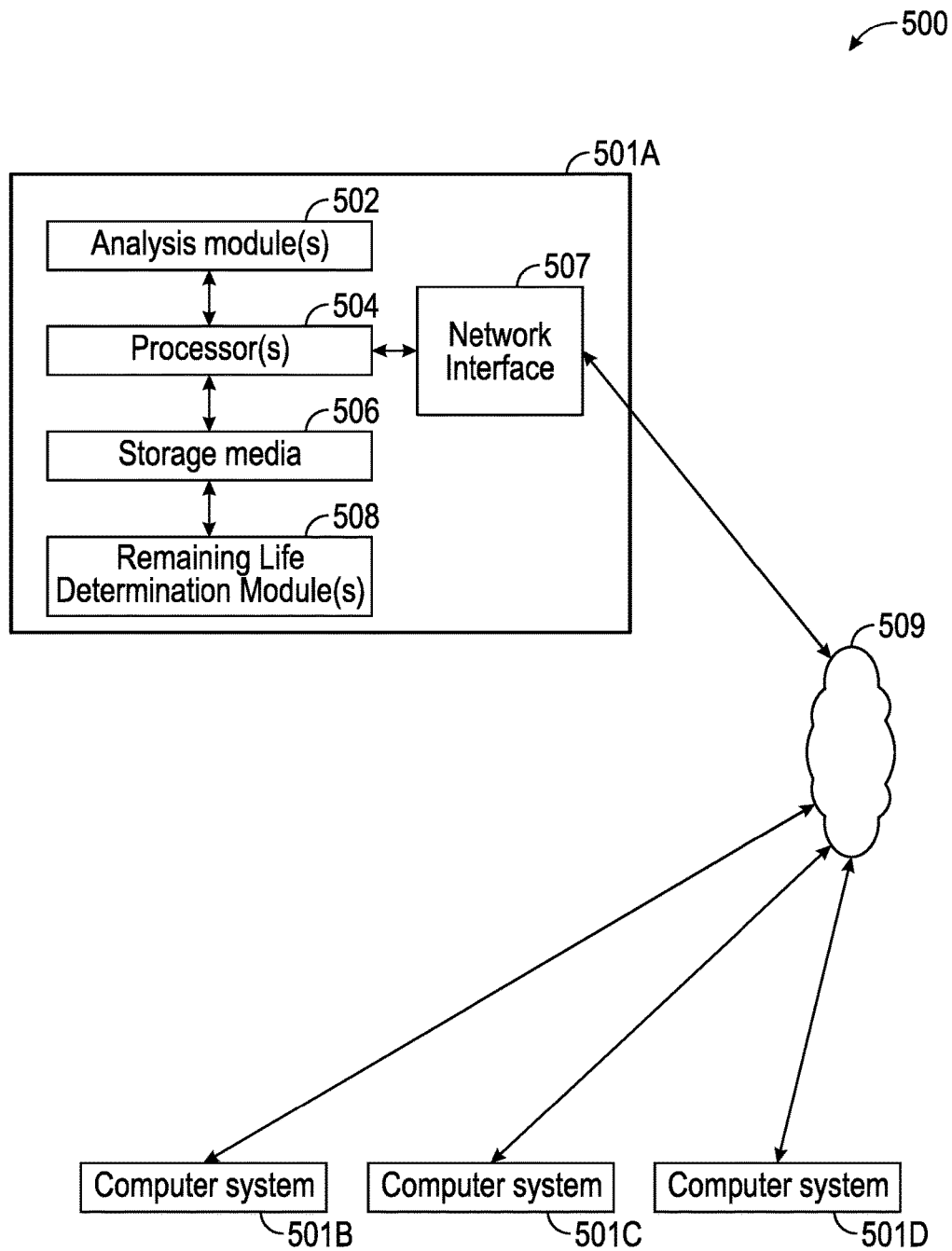
FIG. 5 depicts a computing system for performing the method disclosed herein, according to an embodiment.

In some embodiments, the method 400 may be executed by a computing system. FIG. 5 illustrates an example of such a computing system 500, in accordance with one or more embodiments. At least a portion of the computing system 500 may be located in the downhole tool 130 or at a surface location. The computing system 500 may include a computer or computer system 501A, which may be an individual computer system 501A or an arrangement of distributed computer systems. The computer system 501A includes one or more analysis module(s) 502 configured to perform various tasks according to some embodiments, such as the method 400. To perform these various tasks, the analysis module 502 executes independently, or in coordination with, one or more processors 504, which is (or are) connected to one or more storage media 506. The processor(s) 504 is (or are) also connected to a network interface 507 to allow the computer system 501A to communicate over a data network 509 with one or more additional computer systems and/or computing systems, such as 501B, 501C, and/or 501D (note that computer systems 501B, 501C and/or 501D may or may not share the same architecture as computer system 501A, and may be located in different physical locations, e.g., computer systems 501A and 501B may be located in a processing facility, while in communication with one or more computer systems such as 501C and/or 501D that are located in one or more data centers, and/or located in varying countries on different continents).

A processor can include a microprocessor, microcontroller, processor module or subsystem, programmable integrated circuit, programmable gate array, or another control or computing device.

The storage media 506 can be implemented as one or more computer-readable or machine-readable storage media. Note that while in the example embodiment of FIG. 5 storage media 506 is depicted as within computer system 501A, in some embodiments, storage media 506 may be distributed within and/or across multiple internal and/or external enclosures of computing system 501A and/or additional computing systems. Storage media 506 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories, magnetic disks such as fixed, floppy and removable disks, other magnetic media including tape, optical media such as compact disks (CDs) or digital video disks (DVDs), BLUERAY® disks, or other types of optical storage, or other types of storage devices. Note that the instructions discussed above can be provided on one computer-readable or machine-readable storage medium, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

In some embodiments, computing system 500 contains one or more life span determination module(s) 508. The life span determination module(s) 508 may be configured to perform at least a portion of the method 400.

It should be appreciated that computing system 500 is one example of a computing system, and that computing system 500 may have more or fewer components than shown, the computer system 500 may combine additional components not depicted in the example embodiment of FIG. 5, and/or computing system 500 may have a different configuration or arrangement of the components depicted in FIG. 5. The various components shown in FIG. 5 may be implemented in hardware, software, or a combination of both hardware and software, including one or more signal processing and/or application specific integrated circuits.

Further, the steps in the processing methods described herein may be implemented by running one or more functional modules in information processing apparatus such as general purpose processors or application specific chips, such as ASICs, FPGAs, PLDs, or other appropriate devices. These modules, combinations of these modules, and/or their combination with general hardware are all included within the scope of protection of the disclosure.

As used herein, the terms "inner" and "outer"; "up" and "down"; "upper" and "lower"; "upward" and "downward"; "above" and "below"; "inward" and "outward"; and other like terms as used herein refer to relative positions to one another and are not intended to denote a particular direction or spatial orientation. The terms "couple," "coupled," "connect," "connection," "connected," "in connection with," and "connecting" refer to "in direct connection with" or "in connection with via one or more intermediate elements or members."

While the foregoing is directed to embodiments of the present disclosure, other and further embodiments of the disclosure may be devised without departing from the basic scope thereof.

What is claimed is:

1. A method for determining a remaining life span of an elastomer in a motor, comprising:
   running a downhole tool into a wellbore, the downhole tool including a drill bit and a mud motor, the mud motor having a rotor and a stator, wherein at least one of the rotor or the stator has an elastomer;
   predicting a number of cycles before the elastomer fails;
   determining a number of cycles during a time period;
   determining a change in a remaining life span of the elastomer over the time period, based upon the number of cycles before the elastomer fails and the number of cycles during the time period; and varying a weight on the downhole tool in response to the remaining life span of the elastomer or varying a torque generated by the mud motor in response to the remaining life span of the elastomer.

2. The method of claim 1, wherein predicting the number of cycles before the elastomer fails comprises referencing a library comprising a plurality of measured or simulated values, wherein each of the plurality of measured or simulated values represents a different number of cycles before the elastomer fails.

3. The method of claim 1, further comprising determining the remaining life span of the elastomer at a time based upon a previously determined remaining life span of the elastomer and the change in the remaining life span of the elastomer over the time period.

4. The method of claim 1, wherein the downhole tool further comprises a drill bit, and wherein the method further comprises varying a weight on the drill bit in response to the remaining life span of the elastomer.

5. The method of claim 1, wherein the downhole tool further comprises a drill bit.

6. A method for determining a remaining life span of an elastomer in a motor, comprising:
running a downhole tool into a wellbore, the downhole tool including a mud motor, the mud motor having a rotor and a stator, wherein at least one of the rotor or the stator has an elastomer;
measuring a differential pressure across the mud motor;
measuring a temperature proximate to the mud motor;
determining a number of cycles before the elastomer fails based at least partially upon the differential pressure and the temperature; and
varying a weight on the downhole tool in response to the remaining life span of the elastomer or varying a flow rate of a fluid being pumped into the wellbore in response to the remaining life span of the elastomer.

7. The method of claim 6, wherein determining the number of cycles before the elastomer fails includes selecting, from a library, one of a plurality of measured or simulated values based upon the differential pressure, the temperature, a type of drilling fluid in the wellbore, or a combination thereof, wherein each of the plurality of measured or simulated values represents a different number of cycles before the elastomer fails.

8. The method of claim 6, further comprising measuring the flow rate of the fluid being pumped into the wellbore.

9. The method of claim 8, further comprising determining a number of cycles during a time period based at least partially upon the flow rate.

10. The method of claim 9, further comprising determining a change in a remaining life span of the elastomer over the time period, based upon the number of cycles before the elastomer fails and the number of cycles during the time period.

11. The method of claim 10, further comprising determining the remaining life span of the elastomer at a time based upon a previously determined remaining life span of the elastomer and the change in the remaining life span of the elastomer over the time period.

12. The method of claim 11, wherein the remaining life span of the elastomer at the time is determined without measuring a speed of the mud motor.

13. The method of claim 6, wherein the downhole tool further comprises a drill bit, and wherein the method further comprises varying a weight on the drill bit in response to the remaining life span of the elastomer.

14. The method of claim 6, wherein the downhole tool further comprises a drill bit.

15. A computing system comprising:
one or more processors; and
a memory system comprising one or more non-transitory computer-readable media storing instructions that, when executed by at least one of the one or more processors, cause the computing system to perform operations, the operations comprising:
predicting a number of cycles before an elastomer in a downhole tool fails;
determining a number of cycles during a time period;
determining a change in a remaining life span of the elastomer over the time period, based upon the number of cycles before the elastomer fails and the number of cycles during the time period; and
varying a weight on the downhole tool in response to the remaining life span of the elastomer or varying a flow rate of a fluid being pumped into a wellbore in response to the remaining life span of the elastomer.

16. The computing system of claim 15, wherein predicting the number of cycles before the elastomer fails comprises referencing a library comprising a plurality of measured or simulated values, wherein each of the plurality of measured or simulated values represents a different number of cycles before the elastomer fails.

17. The computing system of claim 15, wherein the operations further comprise determining the remaining life span of the elastomer at a time based upon a previously determined remaining life span of the elastomer and the change in the remaining life span of the elastomer over the time period.

18. The computing system of claim 15, wherein the downhole tool comprises a drill bit, and wherein the operations further comprise varying a weight on the drill bit in response to the remaining life span of the elastomer.

19. The computing system of claim 15, wherein the downhole tool comprises a drill bit.

20. The computing system of claim 15, wherein the computing system is at least partially disposed within the downhole tool.

* * * * *